(12) United States Patent
Pokropinski, Jr. et al.

(10) Patent No.: US 6,881,434 B2
(45) Date of Patent: Apr. 19, 2005

(54) PROCESS FOR MAKING SUTURES HAVING IMPROVED KNOT TENSILE STRENGTH

(75) Inventors: Henry Pokropinski, Jr., South River, NJ (US); Howard Scalzo, Kenilworth, NJ (US); Jerome A Fischer, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 81 days.

(21) Appl. No.: 10/209,202

(22) Filed: Jul. 31, 2002

(65) Prior Publication Data

US 2004/0028805 A1 Feb. 12, 2004

(51) Int. Cl.⁷ .......................... A61L 17/00; A61L 17/14; B05D 3/00
(52) U.S. Cl. ...................... 427/2.31; 427/307; 427/357; 427/412
(58) Field of Search ................................ 427/2.1, 2.31, 427/299, 307, 402, 407.1, 412

(56) References Cited

U.S. PATENT DOCUMENTS

| | | |
|---|---|---|
| 4,027,676 A | 6/1977 | Mattei |
| 4,105,034 A | 8/1978 | Shalaby et al. |
| 4,185,637 A | 1/1980 | Mattei |
| 4,201,216 A * | 5/1980 | Mattei ........................ 606/230 |
| 4,624,256 A | 11/1986 | Messier et al. |
| 4,705,820 A | 11/1987 | Wang et al. |
| 4,791,929 A | 12/1988 | Jarrett et al. |
| 4,844,067 A * | 7/1989 | Ikada et al. ................. 606/231 |
| 4,857,602 A | 8/1989 | Casey et al. |
| 4,994,074 A | 2/1991 | Bezwada et al. |
| 5,100,433 A | 3/1992 | Bezwada et al. |
| 5,312,437 A | 5/1994 | Hermes et al. |
| 5,371,176 A | 12/1994 | Bezwada et al. |
| 5,378,540 A | 1/1995 | Olson |
| 5,425,949 A | 6/1995 | Bennett et al. |
| 5,464,929 A | 11/1995 | Bezwada et al. |
| 5,543,218 A | 8/1996 | Bennett et al. |
| 5,609,609 A | 3/1997 | Ohshima et al. |
| 5,925,065 A | 7/1999 | Totakura et al. |
| 5,939,191 A | 8/1999 | Bennett et al. |
| 5,989,621 A * | 11/1999 | Lichkus et al. ............ 427/2.31 |
| 6,177,094 B1 | 1/2001 | Jiang |

FOREIGN PATENT DOCUMENTS

| | | | |
|---|---|---|---|
| EP | 0 839 541 A2 | 5/1998 | |
| EP | 0908142 | 4/1999 | |
| EP | 0 908 142 A * | 4/1999 | ........... A61B/17/04 |
| EP | 0908142 | 9/1999 | |
| WO | WO 86/0020 | 1/1986 | |

* cited by examiner

*Primary Examiner*—Shrive P. Beck
*Assistant Examiner*—William Phillip Fletcher, III

(57) ABSTRACT

A process for improving the knot tensile strength of a braided suture while maintaining its first throw holding characteristics includes the steps of applying a biocompatible co-polymer to the braided suture and then heating the suture to a temperature above the flow point of the co-polymer. An outer coat is applied to the suture after the heating step. The suture may be scoured with a solvent before the co-polymer is applied or the co-polymer may be applied simultaneously with the scouring step. The co-polymer preferably comprises one or more lactones, more preferably, ε-caprolactone and glycolide. This process may be used with bioabsorbable sutures, such as those comprising filaments made of polyglycolide and polylactide.

18 Claims, 2 Drawing Sheets

PROCESS FOR MAKING SUTURES HAVING IMPROVED KNOT TENSILE STRENGTH

FIELD OF THE INVENTION

The present invention relates generally to processes for making braided sutures. More specifically, the present invention relates to a process for producing a braided suture having improved knot tensile strength.

BACKGROUND OF THE INVENTION

Braided multifilament sutures are commonly used in surgery because of their excellent flexibility and handling properties compared to monofilament sutures of the same material and diameter. It is known in the art that lubricious coatings may be applied as final coatings to the exterior of some types of braided suture to reduce undesirable surface roughness and the excessive tissue abrasion caused thereby, and to improve desirable characteristics, such as the ease of sliding a knot into place, and to increase the tensile strength of the suture. Nevertheless, the coating should not be so lubricious that it jeopardizes the security of the knot, as determined, for example, by the suture's ability to maintain the first throw of the knot.

The tensile strength of a braided suture is of particular concern because of the risk that the suture may break in the incision or wound under tension. The tensile strength of the suture is particularly low at points where the bends of the knot exert additional stress on the braided filaments, increasing the likelihood that the suture will break at the knot as it is tightened. The final coating itself may have an adverse effect on the tensile strength at these points as it tends to bind the filaments, preventing them from moving relative to each other to relieve the tension exerted therein. When a more lubricious coating (i.e., a coating that promotes movement of the fibers) is used, the knot tensile strength of the suture may be improved, but the additional lubrication may degrade the ability of the suture to hold the first throw of the surgeon's knot. Often, an intentional tradeoff is made to obtain an optimal combination of knot tensile strength and the first throw holding characteristic of the suture.

European Patent Publication No. EP 0 908 142 (owned by Ethicon, Inc., Somerville, N.J.), the disclosure of which is incorporated by reference herein, discloses a process for improving the knot tensile strength of a braided suture by tank-coating the surface of the suture with a co-polymer after performing a scouring step (i.e., scouring the suture in an organic solvent), and then heating the suture so that the co-polymer is redistributed among the braided filaments. However, this publication does not address the issue of knot security or disclose the application of a final coat to the suture.

In the foregoing circumstances, there remains a need for a process that will significantly increase the knot tensile strength of a braided suture while preserving the ability of the suture to accept a final coat with the resulting improvement in its desirable properties, especially its first throw holding characteristic.

SUMMARY OF THE INVENTION

A preferred embodiment of the present invention is a process for producing a braided suture having an improved knot tensile strength and an effective first throw holding characteristic. A preferred process includes the steps of applying a biocompatible co-polymer to the braided suture, heating the suture to a temperature above the flow point of the co-polymer, and applying a final, outer coat to the suture. In a more preferred process, the suture is scoured with a solvent before the co-polymer is applied. In another preferred process, the co-polymer is applied simultaneously with the scouring step by scouring the suture in a solution of co-polymer. The preferred co-polymers for this process comprise at least one lactone. More preferably, the co-polymer comprises ε-caprolactone and glycolide, most preferably in a concentration range of about 0.3% to about 0.5% by weight. Another preferred embodiment of the present invention is a process for improving the knot tensile strength of a braided suture by scouring the suture with a solution of a biocompatible co-polymer, and then heating the suture to a temperature above the flow point of the co-polymer. Preferably, the scouring step is performed so as to remove a spin finish coat from the filaments of the suture while simultaneously applying the co-polymer to the filaments' surfaces.

BRIEF DESCRIPTION OF THE DRAWINGS

For a more complete understanding of the present invention, reference is made to the following detailed description of the present invention considered in conjunction with the accompanying drawings, in which.

DETAILED DESCRIPTION OF THE INVENTION

The present invention provides a process for coating filament surfaces with a co-polymer during the fabrication of a braided suture. This process produces a suture that has an increased knot tensile strength compared to conventional sutures prepared according to currently known processes. Moreover, the beneficial effects of a final coat, applied by conventional methods, are preserved, including effective first throw holding characteristics.

Figure 1:
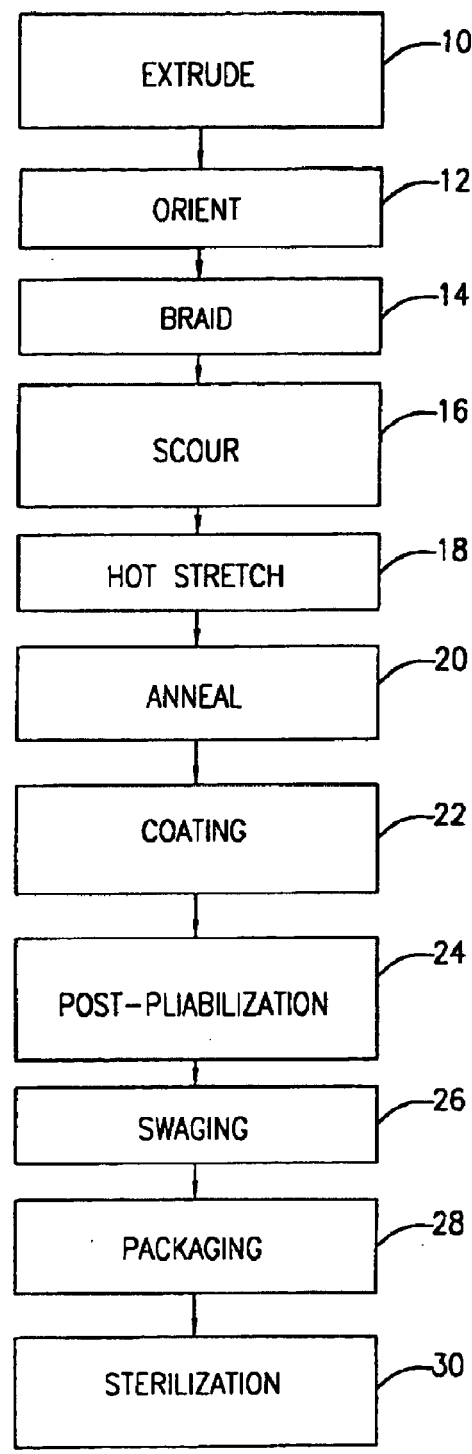
FIG. 1 is a block diagram of a conventional process for manufacturing braided sutures.

FIG. 1 is a block diagram of a suture fabrication process generally employed in the industry. The conditions of each process step may be varied depending on the materials of which a suture is made and the final properties that are desired. Suture filaments are produced in a conventional manner, e.g., by extrusion (see step 10) and orientation of the polymeric structure by a hot stretching process (see step 12), then braided (see step 14) so as to form a suture. During the aforesaid processes, the filaments often are coated with a spin finish, such as a mixture of glycerol monostearate and mineral oil (GMS/MO), that lubricates the filaments to facilitate the handling and processing thereof. The resulting suture is made of a number of very long and finely-drawn filaments that are coated with the spin finish and twisted or braided together. During a subsequent scouring step 16, the spin finish is removed from the filaments by washing the suture in an organic solvent. Typically, the suture is immersed in the solvent as it is pumped through scouring equipment, such as a scouring bath tank. The resulting agitation of the solvent causes it to penetrate throughout the suture, contacting the surface of each of the filaments. The suture is then hot stretched (see step 18) to maximize its elongation, and annealed (see step 20) in a heated chamber for an extended period of time to remove low molecularweight compounds. A final coat, typically comprising selected co-polymers and/or organic salts, is then applied (see step 22) using conventional techniques that are well known in the art. For example, the components of the coating are dissolved/dispersed in a volatile organic solvent to form a coating solution/dispersion and the suture is then immersed in the solution/dispersion in a dip tank or drawn through a coating head to wet the suture with the coating solution/dispersion. The suture is then finished in a conventional manner which may include post-pliabilization (see step 24) wherein the final coat is broken up to increase the pliability of the suture, swaging a needle onto the suture (see step 26), packaging the needle and suture (see step 28) and sterilization of the packaged needle and suture (see step 30).

In a preferred process according to the present invention, the braided suture is coated with a co-polymer prior to being heated, e.g., before the hot stretch step 18 (see FIG. 1). Although the scope of the invention is not limited by any theory, it is believed that heating the suture after applying the co-polymer, i.e., during the subsequent hot stretch and annealing steps 18, 20, further improves the distribution of the co-polymer among the suture filaments, thereby contributing to an increase in knot tensile strength. This coating step, preferably, is performed by immersing the braided suture in a solution of co-polymer at a low concentration (e.g., between 0.1% and 1.5% co-polymer by weight). More preferably, the co-polymer is applied to the suture after the scouring step 16. A final coat may be applied by a conventional process (e.g., see step 22) after the annealing step 20 is completed to improve the desirable properties of the suture, e.g., to improve the first throw holding characteristic of the suture.

The co-polymers used in the coating step are selected for their ability to wet and lubricate the surfaces of the filaments, as well as for their biocompatibility. The co-polymer should preferably have a flow point within the temperature range of the hot stretch or annealing steps 18, 20. Suitable co-polymers are well known within the prior art and, in general, may be selected from those presently used in the final coating step 22 to provide lubricious coatings for the exterior surfaces of braided sutures. The majority of the co-polymers suitable for medical applications can be grouped as aliphatic polyesters derived from polyoxalates and polyoxaesters, as disclosed, e.g., in U.S. Pat. No. 5,464,929; castor oil derivatives, as disclosed, e.g., in U.S. Pat. No. 5,371,176; or caprolactone/glycolide co-polymers, as disclosed, e.g., in U.S. Pat. No. 4,994,074, the disclosures of said patents being incorporated by reference herein. Polyoxaester compounds preferred for use as lubricious coatings include the reaction products of an aliphatic polyoxycarboxylic acid and, at least, a diol (or polydiol), a lactone (or lactone oligomer), a coupling agent, or a combination thereof. More preferably, the polyoxaester compound is a reaction product of ethylene glycol and either 3,6,9-trioxaundecanoic acid, polyglycol diacid, or 3,6-dioxaoctanedioic acid. Preferably, castor oil co-polymers used as lubricious coatings include castor oil and either ε-caprolactone, glycolide or 1,4-dioxanone or combinations thereof. Other lactone-based co-polymers may also be used advantageously as lubricious coatings, as is disclosed in European Patent Publication No. EP 0 908 142, the disclosure of which is incorporated by reference herein. ε-caprolactone, 1,4-dioxanone, 1,4-dioxepan-2-one, 1,5-dioxepan-2-one, trimethylene carbonate, glycolide and lactide are preferred lactones for use in forming lubricious co-polymeric coatings. The more preferred lactones are ε-caprolactone, 1,4-dioxanone and glycolide.

The solvent of the co-polymer solution should preferably be able to dissolve the components of the co-polymer to the desired concentration and be sufficiently volatile that it will be removed from the suture during the subsequent heating steps 18, 20. The solvent should also be chemically compatible with the suture material (i.e., it should not attack or degrade the suture material), although the contact time between the suture and solvent typically is less than a minute. The solvent used for the co-polymer solution may be the same as is used in the scouring step, or a different solvent may be used. The solvent used in the scouring step should preferably be able to dissolve the spin finish and should be chemically compatible with the suture material because the contact time during the scouring step may be 15 minutes or longer.

Another preferred process involves coating the surfaces of the filaments with the selected co-polymer during the performance of the scouring step 16 by scouring the suture with a solution of co-polymer. To facilitate consideration and discussion, the foregoing process step shall be referred to hereinafter as the "scour-coat step" to denote the application of co-polymer to the suture during performance of the scouring step 16. The term "scour-coat" shall also denote the solution of co-polymer in scouring solvent used to apply co-polymer to the suture filaments during the scour-coat step. The scour-coat step is followed by a heating step, e.g., the hot stretch step 18. Surprisingly, scouring the suture and simultaneously applying co-polymer to the suture in a single step process, followed by the step of heating the suture, is observed to be as effective in improving knot tensile strength as scouring the suture and applying the co-polymer as separate steps, followed by the step of heating the suture. Although the scope of the invention is not limited by any theory, it is believed that scouring causes the scour-coat to penetrate throughout the suture, depositing the co-polymer on the surface of each filament at the same time that it dissolves the spin finish. As discussed above, the conventional practice in the industry is to scour the suture with an organic solvent before applying a co-polymeric coating. This is done to prepare the surface of the filaments to become coated with the co-polymer without interference from the spin finish.

The co-polymer used in the scour-coat is selected for its ability to adhere to the surfaces of the filaments in preference to the spin finish in the presence of the scouring solvent. The ability of the co-polymer to wet and lubricate the filaments should also be considered, as well as the biocompatibility of the co-polymer. Suitable co-polymers may be selected from the same groups discussed above, in a similar order of preference. The solvent for the scour-coat is selected for its ability to dissolve the co-polymer to a desired concentration, for its ability to efficiently remove the spin finish from the filament surfaces in preference to the co-polymer, and for its compatibility with the suture material. Chemical compatibility between the solvent and the suture material is particularly important as the contact time in the scour-coat step may be 15 minutes or longer.

As may be appreciated from the foregoing discussion, the optimum scour-coat composition and process conditions for the scour-coat step depend on the selection of a co-polymer, solvent and spin finish that operate together with the material of the suture filaments. The selection of the scour-coat and the conditions of the scour-coat step require some knowledge of polymer chemistry and filament properties, supported by a reasonable amount of experimentation, but are well within the knowledge and skill possessed by the ordinary practitioner in this art. A final coat may be applied to sutures prepared using the scour-coat step using conventional processes and final coat compositions that are known in the industry.

The following illustrative examples are intended to demonstrate the application of the invention to a type of braided suture well-known within the industry and are not intended to limit the scope of the invention in any way. All of the experiments described herein were performed on polyglactin (VICRYL®, Ethicon, Inc., Somerville, N.J.) braided sutures which are made of a bioabsorbable co-polymer comprising 90% polyglycolic acid and 10% polylactide by weight (90/10 PGA/PLA). The sutures were manufactured at laboratory scale according to the standard process steps employed for the commercial VICRYL® braided sutures except for the inclusion of a scour-coat step, or other modifications to the coating steps, as described herein. The final coat dispersion applied to each suture during the final coating step 22 comprised a 9.0% dispersion in ethyl acetate of a 50/50 mixture of calcium stearate and a 65/35 PLA/PGA co-polymer. After the final coating step 22, the sutures were subjected to post-pliabilization (see step 24) and sterilization (see step 30). All ratios and percentages used in the various formulations disclosed herein are presented on a weight-ratio basis.

Figure 2:
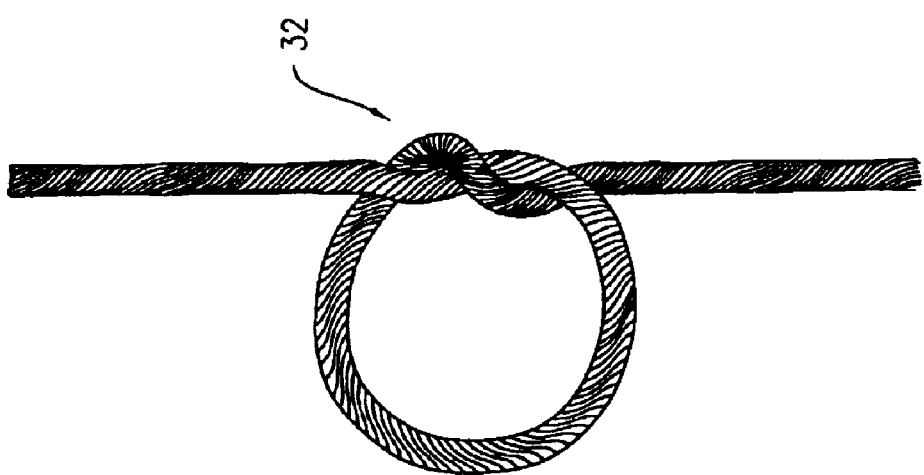
FIG. 2 is an illustration of a single throw knot used to test the knot tensile strength of a suture.

In the following examples, knot tensile strength and straight tensile strength were measured with an INSTRON Tensile Tester (Instron Corp., Canton, Mass.) according to conventional test procedures. Knot tensile strength was evaluated for a simple single-throw knot 32 with the right strand passing "over-under-and-over" the left strand as shown in FIG. 2. The suture was secured in the tensile test device with the knot approximately half-way between the grips.

Figure 3:
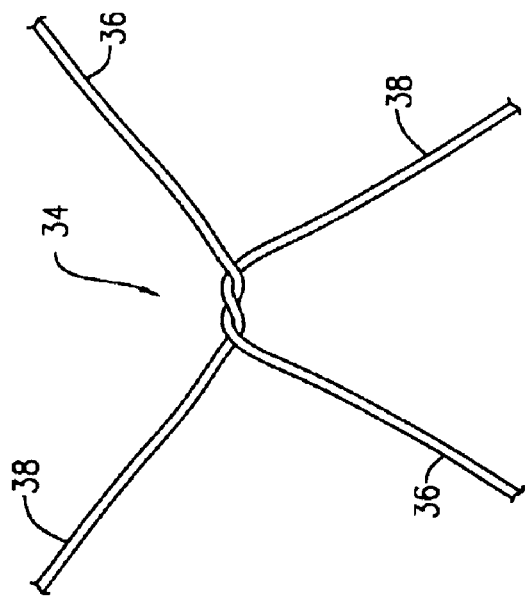
FIG. 3 is an illustration of a "first throw" knot used to test the knot holding characteristics of a suture.

First throw holding properties were ranked by individual surgeons according to their subjective comparisons. Generally, to evaluate the holding properties of a suture, the surgeon passes the suture through the edges of a wound, which may be an incision made in animal tissue or a simulation on a test platform, and ties a single throw knot, or "friction knot", with each suture running "over-under-and-over" the other as shown in the suture configuration 34 of FIG. 3. The strands 36, 38 of the suture are pulled apart to pull the edges of the wound together. When the strands 36, 38 are released, the surgeon evaluates whether the suture holds the edges of the wound together in a satisfactory manner with minimal slippage of the single throw knot 34.

EXAMPLE 1

Effect of the Order of Process Steps on Knot Tensile Strength

A series of tests were performed to examine the knot tensile strengths of VICRYL® braided sutures coated with a mixture of 90% ε-caprolactone and 10% glycolide (90/10 CAP/GLY) in ethyl acetate. Coatings were applied using conventional laboratory equipment according to the process sequences described herein below.

Tests were performed using dyed VICRYL® 2-0 sutures that had been coated according to the following process sequences:

Controls 1 and 2: scour in 100% ethyl acetate, hot stretch, anneal, tank coat with final coat dispersion;

Lot 1: scour in 100% ethyl acetate, tank coat with 0.5% of 90/10 CAP/GLY in ethyl acetate for 10 seconds, hot stretch, anneal, tank coat with final coat dispersion;

Lot 2: scour in 100% ethyl acetate, tank coat with 1.0% of 90/10 CAP/GLY in ethyl acetate for 10 seconds, hot stretch, anneal, tank coat with final coat dispersion;

Lot 3: scour in 0.5% of 90/10 CAP/GLY in ethyl acetate for 15 minutes, hot stretch, anneal, tank coat with final coat dispersion;

Lot 4: scour in 1.0% of 90/10 CAP/GLY in ethyl acetate for 15 minutes, hot stretch, anneal, tank coat with final coat dispersion;

Lot 5: scour in 100% ethyl acetate, hot stretch, anneal, tank coat with a mixture of 0.5% of 90/10 CAP/GLY added to final coat dispersion;

Lot 6: scour in 100% ethyl acetate, hot stretch, anneal, tank coat with a mixture of 1.0% of 90/10 CAP/GLY added to final coat dispersion;

Lot 7: scour in 100% ethyl acetate, hot stretch, anneal, coat with 0.5% of 90/10 CAP/GLY in ethyl acetate using a first coating head, coat with final coat dispersion using a second coating head; and Lot 8: scour in 100% ethyl acetate, hot stretch, anneal, coat with 1.0% of 90/10 CAP/GLY in ethyl acetate using a first coating head, coat with final coat dispersion using a second coating head.

The results of the knot tensile strength tests are summarized in Table 1 below. Test data for Lots 1–4 were compared to data for Control 1, and test data for Lots 5–8 were compared to data for Control 2. In each case, the application of 90/10 CAP/GLY to the suture produced at least some increase in knot tensile strength over that measured for the corresponding control suture. Adding the lubricious material before the hot stretch step (Lots 1–4) resulted in substantially greater increases in knot tensile strength compared to addition of 90/10 CAP/GLY during the final coating step 22 (Lots 5–8). Surprisingly, the results show no apparent difference in the effectiveness of applying the 90/10 CAP/GLY after the scouring step (Lots 1 and 2) and applying it concurrently with the scouring step (Lots 3 and 4). This indicates that, contrary to the practice in the industry, a co-polymer coating may be applied to a suture simultaneously with removing the spin finish.

TABLE 1

Effects of Lubricious Material (90/10 CAP/GLY) on Knot Tensile Strength

| Process Sequence | Knot Tensile Strength (lbs) | Knot Tensile Strength (std dev) | % Change Knot Tensile Strength |
|---|---|---|---|
| Control 1 | 7.79 | 0.27 | — |
| Lot 1 | 9.29 | 0.32 | 19 |
| Lot 2 | 8.95 | 0.64 | 15 |
| Lot 3 | 9.13 | 0.38 | 17 |
| Lot 4 | 9.13 | 0.39 | 17 |
| Control 2 | 7.56 | 0.40 | — |
| Lot 5 | 7.84 | 0.27 | 4 |
| Lot 6 | 8.15 | 0.31 | 8 |
| Lot 7 | 8.01 | 0.31 | 6 |
| Lot 8 | 8.63 | 0.33 | 14 |

Tensile strength = mean tensile strength measured for 10 samples

EXAMPLE 2

Effect of the Order of Process Steps on First Throw Holding Characteristic

Sutures from Lots 1, 3, 6 and 8 of Example 1 above were selected for tests of their knot security as determined by comparison of their first throw holding characteristics. Three sutures from each lot were tested at each of four incision sites in a porcine study.

The subjective ranking of first throw holding characteristics, presented in Table 2 below, show that applying the lubricious coating before the hot stretch and annealing steps 18, 20 (Lots 1 and 3) produces better first throw holding properties than applying the lubricious coating after those steps (Lots 6 and 8). On average, both Lot 1 and Lot 3 were considered to have a first throw holding characteristic equivalent to the control sutures. The sutures from Lots 6 and 8 were consistently considered to have worse first throw holding characteristics than the control. The effectiveness of Lots 1 and 3 in holding the first throw of the knot was somewhat unexpected as it had been believed that providing an additional lubricious coating beneath the final coat would interfere with the contact between the final coat and the filament surfaces, allowing the final coat to slip.

TABLE 2

First Throw Holding Rankings Compared to Control

| Incision Site: | A | | | B | | | C | | | D | | | Average Across Sites |
|---|---|---|---|---|---|---|---|---|---|---|---|---|---|
| Suture: | 1 | 2 | 3 | 4 | 5 | 6 | 7 | 8 | 9 | 10 | 11 | 12 | |
| Lot 1 | 3 | 2 | 2 | 5 | 5 | 3 | 2 | 1 | 1 | 4 | 4 | 4 | 3.0 |
| Lot 3 | 2 | 2 | 3 | 5 | 5 | 5 | 1 | 1 | 1 | 3 | 3 | 3 | 2.8 |
| Lot 6 | 2 | 1 | 1 | 1 | 1 | 1 | 1 | 1 | 1 | 2 | 2 | 2 | 1.3 |
| Lot 8 | 2 | 1 | 1 | 1 | 1 | 1 | 1 | 1 | 1 | 2 | 2 | 2 | 1.3 |

First Throw Rankings:
1 = Worse than control
2 = Slightly worse than control
3 = Equivalent to control
4 = Slightly better than control
5 = Better than control

EXAMPLE 3

Effect of Scour-Coat Step on First Throw Holding Characteristic

Table 3 compares surgeons' ratings of the first throw holding properties of VICRYL® 2-0 standard size sutures prepared with a scour-coat of 0.5% of 90/10 CAP/GLY in ethyl acetate against ratings of the first throw holding properties of similar sutures scoured in 100% ethyl acetate without CAP/GLY. The performance of each suture was rated by 11 surgeons, each performing six ties in a porcine study.

The results of the study show that the sutures prepared with a scour-coat followed by a standard final coat were preferred equally to the sutures prepared with only the standard final coat, based on comparison of the grand average (mean) results of Table 3 below. The mean values of 2.64 for the scour-coat sutures and 2.67 for the sutures with only a final coat would be equivalent to ratings between "fair" and "good" according to the ranking system used in the study. Comparison of the variances of the test populations (Table 4) shows no significant difference in variability between the results obtained for the sutures prepared with the scour-coat and those prepared with only the standard coating.

TABLE 3

Surgeon Preference Study - First Throw Holding

| Surgeon # | Standard Coating First Throw Holding Rating | Scour Coat First Throw Holding Rating |
|---|---|---|
| 1 Average | 2.00 | 2.17 |
| 2 Average | 3.00 | 3.00 |

TABLE 3-continued

Surgeon Preference Study - First Throw Holding

| Surgeon # | Standard Coating First Throw Holding Rating | Scour Coat First Throw Holding Rating |
|---|---|---|
| 3 Average | 2.83 | 2.17 |
| 4 Average | 2.83 | 2.83 |
| 5 Average | 2.50 | 2.50 |
| 6 Average | 2.50 | 2.67 |
| 7 Average | 2.83 | 2.67 |
| 8 Average | 3.00 | 2.67 |
| 9 Average | 2.00 | 3.00 |
| 10 Average | 3.00 | 2.83 |
| 11 Average | 2.83 | 2.50 |
| Grand Average | 2.67 | 2.64 |

First Throw Rankings:
3 = Good
2 = Fair
1 = Poor

TABLE 4

Two-Sample Analysis of Variances (F-test)

| | Standard Coating | Scour Coat |
|---|---|---|
| Mean | 2.667 | 2.636 |
| Variance | 0.287 | 0.266 |
| Observations | 66 | 66 |
| df | 65 | 65 |
| F | 1.081 | |
| P (F <= f) one-tail | 0.378 | |
| F critical one-tail | 1.508 | |

EXAMPLE 4

Scour-Coat Concentration/Suture Size Comparison

The effect of scour-coat concentration on knot tensile strength was investigated for sutures across a range of standard sizes. The tests were performed using standard VICRYL® braided sutures with concentrations of 0.0% up to 1.5% of 90/10 CAP/GLY in ethyl acetate applied during the scour-coat step. The sutures that were scoured with ethyl acetate at 0.0% CAP/GLY concentrations were used as controls for each suture size tested. The values reported in Tables 5–10 below for straight tensile strength and knot tensile strength are the mean values of ten (10) replicate tests performed on sutures treated at each scour-coat concentration indicated therein.

Knot tensile strength increased measurably over that of the control suture at each scour-coat concentration tested for sutures of standard sizes of 3, 0, 2-0, 3-0 and 5-0. The knot tensile strength data show substantial improvements in knot tensile strength for sutures prepared at scour-coat concentrations of 0.3% and above for the same group of sutures. Increasing the scour coat concentrations above 0.5% did not generally result in a commensurate increase in knot tensile strength, but indicated a trend of progressively smaller improvements in knot tensile strength as the scour-coat concentrations were increased. Sutures of size 6-0, the smallest diameter suture tested, showed about the same knot tensile strength as the control across the range of scour coat concentrations tested. Little to no change was observed in straight tensile strength across the ranges of CAP/GLY concentrations applied to each of the suture sizes tested.

The results of this series of tests demonstrate that application of a scour-coat in the concentration range of 0.1% to 1.5% of 90/10 CAP/GLY increases the knot tensile strength of VICRYL® braided sutures of size 5-0 and larger. A concentration range of 0.2% to 1.0% is more preferred, and an optimum concentration range of 0.3% to 0.5% is indicated.

TABLE 5

Scour-Coating Concentration Tests
(Size 3 VICRYL® braided suture)

| Scour-Coat Concentration | Straight Tensile Strength (lbs) | Straight Tensile Strength (std dev) | Knot Tensile Strength (lbs) | Knot Tensile Strength (std dev) | % Change Knot Tensile Strength |
|---|---|---|---|---|---|
| 0.0% | 50.950 | 0.896 | 27.671 | 1.422 | — |
| 0.1% | 49.564 | 0.485 | 29.340 | 1.353 | 6.3 |
| 0.2% | 50.772 | 0.776 | 29.886 | 1.476 | 8.0 |
| 0.3% | 49.238 | 0.673 | 30.984 | 0.865 | 12.0 |
| 0.5% | 48.502 | 0.720 | 30.921 | 0.609 | 11.7 |
| 0.7% | 48.881 | 0.767 | 32.007 | 0.690 | 15.7 |
| 1.0% | 48.773 | 0.729 | 30.959 | 1.525 | 11.9 |

TABLE 6

Scour-Coating Concentration Tests
(Size 0 VICRYL® braided suture)

| Scour-Coat Concentration | Straight Tensile Strength (lbs) | Straight Tensile Strength (std dev) | Knot Tensile Strength (lbs) | Knot Tensile Strength (std dev) | % Change Knot Tensile Strength |
|---|---|---|---|---|---|
| 0.0% | 22.627 | 0.493 | 11.989 | 0.362 | — |
| 0.1% | 22.381 | 0.458 | 12.312 | 0.557 | 2.7 |
| 0.3% | 21.744 | 0.506 | 12.763 | 0.442 | 6.5 |
| 0.5% | 22.092 | 0.704 | 13.253 | 0.666 | 10.4 |
| 0.7% | 22.063 | 0.416 | 13.298 | 0.471 | 10.9 |
| 1.0% | 21.720 | 0.564 | 12.996 | 0.691 | 8.4 |

TABLE 7

Scour-Coating Concentration Tests
(Size 2-0 VICRYL® braided suture)

| Scour-Coat Concentration | Straight Tensile Strength (lbs) | Straight Tensile Strength (std dev) | Knot Tensile Strength (lbs) | Knot Tensile Strength (std dev) | % Change Knot Tensile Strength |
|---|---|---|---|---|---|
| 0.0% | 15.433 | 0.358 | 7.151 | 0.334 | — |
| 0.1% | 15.072 | 0.554 | 7.881 | 0.375 | 10.2 |
| 0.3% | 14.847 | 0.487 | 8.535 | 0.521 | 19.4 |
| 0.5% | 15.084 | 0.486 | 8.589 | 0.530 | 20.1 |
| 0.7% | 15.454 | 0.279 | 8.730 | 0.245 | 22.1 |
| 1.0% | 15.188 | 0.389 | 8.820 | 0.473 | 23.4 |
| 1.5% | 15.006 | 0.496 | 8.935 | 0.304 | 25.0 |

TABLE 8

Scour-Coating Concentration Tests
(Size 3-0 VICRYL® braided suture)

| Scour-Coat Concentration | Straight Tensile Strength (lbs) | Straight Tensile Strength (std dev) | Knot Tensile Strength (lbs) | Knot Tensile Strength (std dev) | % Change Knot Tensile Strength |
|---|---|---|---|---|---|
| 0.0% | 9.399 | 0.272 | 5.011 | 0.268 | — |
| 0.1% | 8.952 | 0.450 | 5.241 | 0.178 | 4.6 |
| 0.2% | 9.482 | 0.316 | 5.558 | 0.257 | 10.9 |
| 0.3% | 9.321 | 0.259 | 5.569 | 0.254 | 11.1 |
| 0.5% | 9.092 | 0.244 | 5.633 | 0.249 | 12.4 |
| 0.7% | 9.064 | 0.223 | 5.621 | 0.203 | 12.2 |
| 1.0% | 9.279 | 0.226 | 5.540 | 0.102 | 10.6 |

TABLE 9

Scour-Coating Concentration Tests
(Size 5-0 VICRYL® braided suture)

| Scour-Coat Concentration | Straight Tensile Strength (lbs) | Straight Tensile Strength (std dev) | Knot Tensile Strength (lbs) | Knot Tensile Strength (std dev) | % Change Knot Tensile Strength |
|---|---|---|---|---|---|
| 0.0% | 3.591 | 0.081 | 1.872 | 0.068 | — |
| 0.1% | 3.472 | 0.079 | 2.044 | 0.091 | 9.2 |
| 0.3% | 3.668 | 0.178 | 2.074 | 0.095 | 10.8 |
| 0.5% | 3.568 | 0.089 | 2.088 | 0.117 | 11.5 |
| 0.7% | 3.695 | 0.199 | 2.146 | 0.118 | 14.6 |
| 1.0% | 3.523 | 0.121 | 2.090 | 0.083 | 11.6 |

TABLE 10

Scour-Coating Concentration Tests
(Size 6-0 VICRYL® braided suture)

| Scour-Coat Concentration | Straight Tensile Strength (lbs) | Straight Tensile Strength (std dev) | Knot Tensile Strength (lbs) | Knot Tensile Strength (std dev) | % Change Knot Tensile Strength |
|---|---|---|---|---|---|
| 0.0% | 1.788 | 0.042 | 1.000 | 0.067 | — |
| 0.1% | 1.687 | 0.121 | 0.981 | 0.107 | -1.9 |
| 0.3% | 1.745 | 0.083 | 1.041 | 0.081 | 4.1 |
| 0.5% | 1.674 | 0.104 | 1.002 | 0.074 | 0.2 |
| 0.7% | 1.685 | 0.088 | 1.044 | 0.076 | 4.4 |
| 1.0% | 1.587 | 0.094 | 0.962 | 0.075 | -3.8 |
| 1.5% | 1.709 | 0.091 | 1.005 | 0.065 | 0.5 |

Although the invention disclosed herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the invention as defined by the appended claims.

We claim:

1. A process for treating a braided suture, comprising the steps of:
    scouring the braided suture with a solution of a biocompatible co-polymer in a solvent, wherein said scouring simultaneously removes residue from the braided suture and applies a first coating of said co-polymer to the braided suture;
    heating the braided suture at a temperature above the flow point of said co-polymer; and
    applying a second coating to the braided suture,
    wherein the heating step is performed after the scouring step and before the step of applying the second coating.
2. The process of claim 1, wherein said co-polymer comprises at least one compound selected from the group consisting of ε-caprolactone, 1,4-dioxanone, 1,4-dioxapan-2-one, trimethylene carbonate, glycolide and lactide.

3. The process of claim 2, wherein said co-polymer comprises ε-caprolactone and glycolide.

4. The process of claim 3, wherein said co-polymer comprises ε-caprolactone and glycolide in a proportion of about 90% ε-caprolactone to about 10% glycolide by weight.

5. The process of claim 1, wherein said second coating is an outer coating.

6. A process for treating a braided suture which includes a plurality of filaments, said process comprising the steps of:
   scouring the braided suture with a solution of a biocompatible co-polymer wherein said scouring applies a coating of the co-polymer to the filaments of the braided suture; and
   heating the braided suture at a temperature above the flow point of the co-polymer after the performance of the scouring step.

7. The process of claim 6, wherein the filaments of the braided suture have a spin finish coating prior to the performance of said scouring step, said scouring step including simultaneously removing the spin finish coating from the filaments as said co-polymer is applied thereto.

8. The process of claim 7, wherein the spin finish coating comprises glycerol monostearate and mineral oil and said solution comprises ethyl acetate.

9. The process of claim 6, wherein said co-polymer comprises at least one compound selected from the group consisting of ε-caprolactone, 1,4-dioxanone, 1,4-dioxapan-2-one, trimethylene carbonate, glycolide and lactide.

10. The process of claim 9, wherein said co-polymer comprises ε-caprolactone and glycolide.

11. The process of claim 10, wherein said co-polymer comprises ε-caprolactone and glycolide in a proportion of about 90% ε-caprolactone to about 10% glycolide by weight.

12. The process of claim 11, wherein said co-polymer is applied in a solution comprising between about 0.1% and about 1.5% co-polymer by weight.

13. The process of claim 12, wherein said co-polymer is applied in a solution comprising between about 0.2% and about 1.0% co-polymer by weight.

14. The process of claim 13, wherein said co-polymer is applied in a solution comprising between about 0.3% and about 0.5% co-polymer by weight.

15. The process of claim 6, wherein the braided suture is made from a bioabsorbable material.

16. The process of claim 15, wherein the bioabsorbable material comprises a polyglycolide and polylactide.

17. The process of claim 16, wherein the bioabsorbable material comprises a polyglycolide and a polylactide in a proportion of about 90% polyglycolide to about 10% polylactide by weight.

18. The process of claim 6, further comprising the step of applying an outer coating to the braided suture after the heating step, wherein said co-polymer is a first co-polymer and said outer coating includes calcium stearate and a second co-polymer, wherein said second co-polymer comprises a polylactide and a polyglycolide in a proportion of about 65% polylactide to about 35% polyglycolide by weight.

* * * * *